(12) United States Patent
Ansmann et al.

(10) Patent No.: US 6,677,486 B2
(45) Date of Patent: Jan. 13, 2004

(54) HYDROGENATION OF NITRILES OVER RANEY CATALYSTS

(75) Inventors: Andreas Ansmann, Wiesloch (DE); Christoph Benisch, Eppelheim (DE); Frank Funke, Frankenthal (DE); Frank Ohlbach, Düsseldorf (DE); Martin Merger, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/985,982

(22) Filed: Nov. 7, 2001

(65) Prior Publication Data

US 2002/0058841 A1 May 16, 2002

(30) Foreign Application Priority Data

Nov. 16, 2000 (DE) .......................................... 100 56 839

(51) Int. Cl.[7] .............................. C07C 29/48; B01J 21/04
(52) U.S. Cl. ........................ 564/490; 564/415; 564/491; 564/492; 564/493; 502/301
(58) Field of Search ................................. 564/415, 490, 564/491, 492, 493; 502/301

(56) References Cited

U.S. PATENT DOCUMENTS 4,826,799 A * 5/1989 Cheng et al. ................ 502/301
6,121,188 A * 9/2000 Breitscheidel et al. ...... 502/301
6,337,300 B1 * 1/2002 Sauer et al. ................. 502/301
6,469,211 B2 * 10/2002 Ansmann et al. ........... 564/415

FOREIGN PATENT DOCUMENTS

EP  0 880 996 A1 * 12/1998 ............ B01J/25/00

* cited by examiner

*Primary Examiner*—Brian Davis
(74) *Attorney, Agent, or Firm*—Keil & Weinkauf

(57) ABSTRACT

Nitriles are hydrogenated to primary amines over an activated, alpha-$Al_2O_3$-containing, macroporous Raney catalyst based on an alloy of aluminum and at least one transition metal selected from the group consisting of iron, cobalt and nickel, and, if desired, one or more further transition metals selected from the group consisting of titanium, zirconium, chromium and manganese, which is obtainable by a process comprising the steps in the order (a)–(f):

(a) preparing a kneadable composition comprising the alloy, a shaping aid, water and a pore former;
(b) shaping the kneadable composition to form a shaped body;
(c) calcining the shaped body;
(d) activating the calcined shaped body by treatment with aqueous alkali metal hydroxide solution;
(e) rinsing the shaped catalyst body with aqueous alkali metal hydroxide solution;
(f) rinsing the shaped catalyst body with water.

14 Claims, No Drawings

HYDROGENATION OF NITRILES OVER RANEY CATALYSTS

The present invention relates to a process for hydrogenating nitrites to primary amines over an activated macroporous Raney catalyst, to a process for producing the Raney catalysts and to the Raney catalysts themselves.

It is known that nitrites and iminonitriles can be hydrogenated in the liquid phase over Raney catalysts.

EP-A-0 382 508 describes the semicontinuous hydrogenation of polynitriles in the liquid phase over Raney cobalt catalysts in the presence of anhydrous ammonia.

U.S. Pat. No. 5,869,653 describes a continuous process for hydrogenating nitrites over Raney cobalt catalysts in the absence of ammonia, which is carried out in the presence of catalytic amounts of lithium hydroxide and water.

U.S. Pat. No. 4,895,994 discloses a Raney catalyst having a BET surface area of from 20 to 80 m$^2$/g and a proportion of macropores of from 0.01 to 70% by volume, based on the total pore volume, which is produced by mixing the Raney alloy with a high molecular weight polymer, shaping the mixture to form a shaped body, calcining the composition firstly at from 300 to 700° C. and subsequently at from 850 to 1200° C. in the presence of oxygen and leaching aluminum from the calcined shaped body by treatment with 6 N NaOH at from 90 to 100° C. The catalyst which has been activated in this way is subsequently washed repeatedly with water until the pH of the washings is <9. The Raney catalyst is used, inter alia, for hydrogenating nitrites to amines.

EP-A-0 842 699 discloses a process for producing an activated, metal powder-free, macroporous fixed-bed metal catalyst of the Raney type based on an alloy of aluminum and at least one metal of transition group VIII of the Periodic Table, which comprises the steps (1) preparing a kneadable composition comprising the alloy, a shaping aid, water and a pore former, (2) shaping the kneadable composition to give a shaped body, (3) calcining the shaped body and (4) treating the calcined shaped body with an alkali metal hydroxide. After treatment of the shaped body with alkali metal hydroxide, the activated catalyst is washed with water until the pH of the washings has dropped to 7.5. The catalyst obtained in this way has a macropore content of more than 80% by volume. The catalyst is used for hydrogenating nitrites to primary amines.

Such a process is also disclosed in DE-A 44 46 907, in which polyvinyl alcohol and water or stearic acid are used as auxiliaries.

A disadvantage of the Raney catalysts of the prior art is that they have aluminum oxides and aluminum hydroxides having acidic and/or basic properties, e.g. Al(OH)$_3$, AlOOH or $\gamma$-Al$_2$O$_3$, on their surface and these can lead to secondary reactions in the hydrogenation of the nitrites. Examples of such secondary reactions are dissociation of the nitrile or an amine-imine condensation. Particularly for extender nitrites which are obtainable by addition of formaldehyde and hydrocyanic acid onto nucleophilic centers or Michael nitrites which are obtainable by addition of acrylonitrile onto nucleophilic centers, the hydrogenation has to be carried out under particularly gentle conditions since these nitrites are unstable and can be redissociated into their starting materials. In addition, some of the Raney catalysts described have a relatively low proportion of macropores, e.g. the catalysts described in U.S. Pat. No. 4,895,994, which has an adverse effect on mass transfer in the catalyst.

It is an object of the present invention to provide a process for the gentle hydrogenation of nitrites which displays high selectivity in respect of the formation of primary amines and in which secondary reactions such as dissociation of the nitrites are avoided.

We have found that this object is achieved by a process for hydrogenating nitrites to primary amines over an activated, alpha-Al$_2$O$_3$-containing, macroporous Raney catalyst based on an alloy of aluminum and at least one transition metal selected from the group consisting of iron, cobalt and nickel, and, if desired, one or more further transition metals selected from the group consisting of titanium, zirconium, chromium and manganese, which is obtainable by a process comprising the steps in the order (a)–(f):

(a) preparing a kneadable composition comprising the alloy, a shaping aid, water and a pore former;
(b) shaping the kneadable composition to form a shaped body;
(c) calcining the shaped body;
(d) activating the calcined shaped body by treatment with aqueous alkali metal hydroxide solution;
(e) rinsing the shaped catalyst body with aqueous alkali metal hydroxide solution;
(f) rinsing the shaped catalyst body with water.

The object is also achieved by a process for producing the macroporous Raney catalyst and by the macroporous Raney catalyst itself.

The production of the Raney catalyst used according to the present invention is described in more detail below.

According to the present invention, a kneadable composition is firstly prepared from an alloy of aluminum and at least one transition metal selected from the group consisting of iron, cobalt and nickel, and, if desired, one or more further transition metals selected from the group consisting of titanium, zirconium, chromium and manganese, a shaping aid, water and a pore former. Preferred transition metals are nickel and cobalt, and particular preference is given to solid solutions of nickel in cobalt or of cobalt in nickel in which the dissolved metal is present in a concentration of from 0.05 to 50% by weight. To increase the activity and selectivity, the alloy may further comprise at least one additional transition metal selected from the group consisting of titanium, zirconium, chromium and manganese as promoter, generally in concentrations of from 0.01 to 15% by weight, preferably from 0.05 to 5% by weight, based on the total amount of transition metals. The weight ratio of aluminum to transition metals is generally in the range from 30 to 70% by weight of aluminum and from 30 to 70% by weight of transition metal.

The aluminum alloy is produced in a manner known per se, for example as described in DE 21 59 736, whose contents relating to the production of alloys of aluminum and the specified transition metals is hereby incorporated by reference into the present application.

As shaping aids, it is possible to use all shaping aids used in the prior art as are mentioned, for example, in the U.S. Pat. Nos. 4,826,799 and 4,895,994. Preference is given to using waxes such as wax C micropowder PM from HOECHST AG, fats such as magnesium or aluminum stearates, or carbohydrate-containing polymers such as Tylose (methylcellulose); particular preference is given to using stearic acid and Tylose. The amount of shaping aid present in the kneadable composition is generally from about 0.1 to about 3% by weight, preferably from about 0.2 to about 2% by weight, more preferably from about 0.5 to about 1% by weight.

As pore formers, it is possible to use any polymers which have a molar mass of from greater than 6000 to about 500,000 g/mol. Their molar mass is preferably from about 10,000 to about 200,000 g/mol, more preferably from about 13,000 to about 150,000 g/mol and in particular from about 13,000 to about 50,000 g/mol.

Examples of polymers which can be used as pore formers in the process of the present invention are polyvinyl chloride, copolymers of an olefin with polar comonomers, e.g. ethylene or propylene with polyvinyl chloride, polyvinylidene chloride copolymers, ABS polymers, polyethylene copolymers with vinyl acetate, alkylacrylates, acrylic acid, chlorinated polyethylenes, chlorosulfonated polyethylenes, thermoplastic polyurethanes, polyamides such as nylon-5, nylon-12, nylon-6/6, nylon-6/10, nylon-11, fluorine-containing plastics such as FEP, polyvinylidene fluoride, polychlorotrifluoroethylene, acrylonitrile-methyl (meth) acrylate copolymers, acrylonitrile-vinyl chloride copolymers, styrene-acrylonitrile copolymers, methacrylonitrile-styrene copolymers, polyalkyl (meth) acrylates, cellulose acetate, cellulose acetate butyrate, polycarbonates, polysulfones, polyphenylene oxide, polyesters such as butylene terephthalate, and polyvinyl alcohol, with particular preference being given to polyvinyl alcohol. Polyethylene oxides and potato starch are also possibilities.

The amount of pore former present in the kneadable composition is from about 1 to about 20% by weight, preferably from about 4 to about 8% by weight, in each case based on the total weight of the kneadable composition.

The kneadable composition comprising the alloy, the shaping aid, water and the pore former is shaped to form shaped bodies, with pellets and extrudates being preferred. Processing to produce the shaped bodies is carried out in apparatuses known for this purpose, for example in screw extruders, ram extruders or tableting pressers.

In general, the alloy is firstly mixed with the shaping aid and the usually solid polymer as pore former and water is subsequently added a little at a time until a readily shapable, plastic composition is obtained. Such kneadable compositions are produced using the customarily used mixing or kneading apparatuses.

In a particular embodiment, extrudates having a diameter of 3.0 mm are produced and are generally allowed to undergo partial drying at room temperature after being extruded from the extruder. They are subsequently dried at from 80 to 200° C. for from 12 to 24 hours.

Calcination of the shaped bodies is preferably carried out as a particularly gentle three-stage calcination process at atmospheric pressure. Here, the shaped bodies are preferably firstly treated at from about 400 to about 500° C. for from 1 to 3 hours, then at from about 700 to about 800° C. for from 1 to 3 hours and subsequently at from about 900 to about 1000° C. for from 1 to 3 hours. Calcination is usually carried out in air.

The calcined shaped bodies are, according to the present invention, activated using an alkali metal hydroxide, preferably lithium hydroxide, sodium hydroxide, potassium hydroxide or cesium hydroxide or a mixture thereof, particularly preferably using sodium hydroxide alone or in admixture with the abovementioned alkali metal hydroxides. In general, use is made of aqueous solutions of the alkali metal hydroxide, preferably aqueous sodium hydroxide solution, with the alkali metal hydroxide solution having a concentration of from 5 to 30% by weight, preferably from 15 to 25% by weight. The molar ratio of alkali metal hydroxide to aluminum is generally from about 1:1 to about 5:1, preferably from about 1.5:1 to about 3:1.

The activation temperature is usually from about 25° C. to about 106° C., preferably from about 45° C. to about 90° C. The activation time depends essentially on the desired final aluminum content and is generally in the range from 1 to 10 hours, preferably from 2 to 5 hours. The activation procedure can also be carried out a number of times.

After the activation, the shaped catalyst body is rinsed with aqueous alkali metal hydroxide solution and subsequently with water. It is essential that the shaped catalyst body is rinsed with aqueous alkali metal hydroxide solution before being rinsed with water.

In general, rinsing is carried out using an aqueous solution of the alkali metal hydroxide having a concentration of from 5 to 30% by weight, preferably from 15 to 25% by weight. In a preferred embodiment of the invention, rinsing is carried out using the same alkali metal hydroxide used in the activation of the catalyst and the alkali metal hydroxide concentration of the rinsing solution is the same as that of the alkali metal hydroxide solution used for activation. Rinsing is preferably carried out at room temperature. Rinsing with alkali metal hydroxide solution can be carried out a number of times and is preferably carried out three times, with the total amount of alkali metal hydroxide solution used being similar to that used in the activation. Only then is rinsing with water carried out, preferably until the pH of the washings is about 8.

The catalysts produced in this way have an alpha-$Al_2O_3$ content of generally >0.1% by weight, preferably >1.0% by weight.

The washed, activated shaped catalyst bodies are stored under water, preferably in a mixture of water and methanol.

The shaped catalyst bodies produced in this way have a macropore volume of at least 0.1 ml/g, preferably 0.1–0.5 ml/g, a proportion of macropores of at least 80% by volume, preferably from 85 to 95% by volume, based on the total pore volume, and a specific surface area of $\leq 20$ $m^2/g$, preferably from 10 to 20 $m^2/g$. For the purposes of the present invention, macropores are pores having a diameter of $\geq 50$ nm.

According to the present invention, any nitrites can be hydrogenated to give the corresponding primary amines. Nitriles preferred for hydrogenation by the process of the present invention are extender nitriles and nitriles which can be obtained by Michael addition, having the formula (I) or (II)

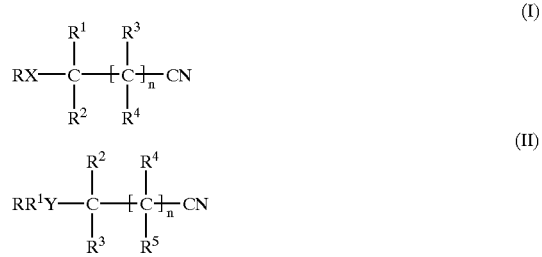

where
X is O or S,
Y is N or P,
n is 0 or 1
and
R, $R^1$, $R^2$, $R^3$, $R^4$, $R^5$ are each, independently of one another, H or a substituted or unsubstituted alkyl radical having 1–10 carbon atoms or a substituted or unsubstituted aryl radical having 6–12 carbon atoms.

Examples are iminodiacetonitrile, nitrilotriacetonitrile, ethylenediaminetetraaceto-nitrile, biscyanoethylpiperazine, dimethylaminopropionitrile, dimethylaminopropylaminopropionitrile and methoxypropionitrile.

Further preferred nitriles are cyclic iminonitriles and acyclic iminonitriles of the formulae (III) and (IV)

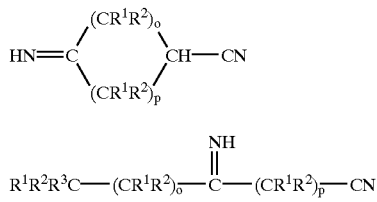

(III)

(IV)

where

R$^1$, R$^2$ and R$^3$ are each, independently of one another, H or a substituted or unsubstituted alkyl radical having 1–10 carbon atoms or a substituted or unsubstituted aryl radical having 6–12 carbon atoms and o,p are each 0, 1, 2, 3, 4 or 5.

An example is isophoronenitrilimine.

Further important nitriles and aminonitriles which can be hydrogenated by the process of the present invention are the compounds (V) to (XXXII) below:

The hydrogenation can be carried out in the gas phase, with or without solvent, continuously as a fixed-bed reaction using a fixed-bed catalyst, for example in the upflow or downflow mode, or as a fluidized-bed reaction using a catalyst which is in upward and downward fluidized motion. Preference is given to using a fixed bed. Dinitriles or polynitriles can also be partially hydrogenated. Altering the residence time enables the conversion and thus the product ratios of amines to aminonitriles to be set in a targeted manner.

The hydrogenation can be carried out over a fixed catalyst bed. Suitable reactors for hydrogenation over a fixed bed are tube reactors. The temperature is generally from 25 to 125° C., and the hydrogen pressure is generally from 10 to 300 bar. The nitrites to be hydrogenated may be present as a solution in an organic solvent. Preferred organic solvents are aliphatic alcohols, amines, amides such as N-methylpyrrolidone and dimethylformamide, ethers and esters. The space velocity over the catalyst is generally from 0.5 to 20, preferably from 2 to 10, mol of nitrile/$l_{catalyst}$*h. Hydrogenation over a fixed bed can be carried out in the presence of ammonia. The ammonia content is generally from 6 to 60, preferably from 12 to 36, mol of ammonia per mol of the nitrile to be hydrogenated.

The invention is illustrated by the following examples.

EXAMPLES

Example 1

Production of a Doped Aluminum-cobalt Fixed-bed Catalyst

A mixture of 900 g of a powder consisting of an alloy of 49.1% by weight of aluminum, 47% by weight of cobalt, 1.5% by weight of chromium, 1.7% by weight of nickel and 0.28% by weight of iron, 80 g of polyvinyl alcohol having a molar mass of from 9000 to 18,000 g/mol and 8 g of Tylose (H2000 P from Clariant) is placed in a kneader and 130 ml of water are added a little at a time. After a kneading time of 3 hours, the plastic composition is shaped on a ram extruder at a pressing pressure of 14 MPa to give 3 mm extrudates. The extrudates are air-dried for 16 hours, then dried at 120° C. for 16 hours and subsequently calcined at 450° C. for 1 hour, at 750° C. for 1 hour and at 900° C. for 2 hours. The extrudates are then crushed to form granules having a particle size of 1.5–4 mm. 300 g of granules are added to 4 l of 20% strength by weight aqueous sodium hydroxide solution at 70° C. After evolution of hydrogen has abated after about 1 hour, the mixture is heated to 90° C. and maintained at this temperature for 3 hours. The catalyst which has been activated in this way is separated from the aqueous sodium hydroxide used for the activation by decantation. 1000 ml of fresh 20% strength by weight aqueous sodium hydroxide are then added to the catalyst at room temperature. After stirring for 5 minutes, the solution is decanted off again. This washing with aqueous sodium hydroxide is repeated twice more. The catalyst is subsequently washed with water until the washings have a pH of about 8.

This gives a catalyst having a specific surface area by the BET method of 18.3 m$^2$/g, a pore volume of 0.26 ml/g, a proportion of macropores of 94% by volume and an $\alpha$-Al$_2$O$_3$ content of >1% by weight.

Example 2

Hydrogenation of Imidodiacetonitrile to Diethylenetriamine 120 g of the moist catalyst produced as described in example 1 are installed in a continuously operated 100 ml laboratory reactor and the reactor is flushed with nitrogen. The reactor is subsequently flooded with 40 bar of ammonia. 20 standard l/h of hydrogen and 18 g/h of ammonia are injected to 100 bar. The temperature is subsequently increased to 60° C. and the pressure is increased to 200 bar. 0.05 kg/h of imidodiacetonitrile, used as a 20% strength by weight solution in N-methylpyrrolidone, is hydrogenated per liter of catalyst. At a conversion of 99%, 89% by weight of diethylenetriamine are formed. The main by-product is 7% by weight of piperazine.

Example 3

Hydrogenation of Biscyanoethylpiperazine to Bisaminopropylpiperazine 120 g of the moist catalyst produced as described in example 1 are installed in a continuously operated 100 ml laboratory reactor and the reactor is flushed with nitrogen. The reactor is subsequently flooded with 40 bar of ammonia, and 100 standard l/h of hydrogen and 51 g/h of ammonia are injected to 65 bar. The temperature is increased to 80° C. 0.15 kg/h of biscyanoethylpiperazine, used as a 50% strength by weight solution in water, is hydrogenated per liter of catalyst. At a conversion of 99.5%, 97.2% by weight of bisaminopropylpiperazine are formed. The main by-products are the mononitrile (0.5% by weight) and aminopropylpiperazine (1.2% by weight).

At a throughput of 0.2 kg/l (catalyst)*h and a hydrogenation temperature of 100° C., 95.8% by weight of bisaminopropylpiperazine are obtained at a conversion of 97.7%. The main by-products are the mononitrile (1.5% by weight) and aminopropylpiperazine (0.7% by weight).

Example 4

Hydrogenation of Isophoronenitrile to Isophoronediamine

In a continuously operated laboratory apparatus comprising a first reactor charged with 100 ml of Al$_2$O$_3$ (4 mm extrudates) and a second reactor charged with 240 g (200 ml) of the Raney catalyst produced as described in example 1, 32 ml/h of isophoronenitrile are hydrogenated by means of 300 ml/h of H$_2$ in the presence of 147 ml/h of NH$_3$ at 250° C. and a pressure of 250 bar. The space velocity over the catalyst is 0.15 kg/l (catalyst)*h, and the residence time is 44 minutes. At a conversion of 99.2%, isophoronediamine is obtained with a selectivity of 89.5%. The cis/trans isomer ratio is 79:21.

We claim:

1. A process for hydrogenating nitrites to primary amines over an activated, alpha-Al$_2$O$_3$-containing, macroporous Raney catalyst based on an alloy of aluminum and at least one transition metal selected from the group consisting of iron, cobalt and nickel, and, if desired, one or more further transition metals selected from the group consisting of titanium, zirconium, chromium and manganese, which is obtainable by a process comprising the steps in the order (a)–(f):

(a) preparing a kneadable composition comprising the alloy, a shaping aid, water and a pore former;

(b) shaping the kneadable composition to form a shaped body;

(c) calcining the shaped body;

(d) activating the calcined shaped body by treatment with aqueous alkali metal hydroxide solution;

(e) rinsing the shaped catalyst body with aqueous alkali metal hydroxide solution;

(f) rinsing the shaped catalyst body with water.

2. A process as claimed in claim 1, wherein the catalyst has been produced on the basis of an alloy of aluminum and a solid solution of nickel in cobalt or of cobalt in nickel which comprises 0.05–50% by weight of the dissolved metal and, if desired, from 0.05 to 5% by weight of one or more of the further transition metals.

3. A process as claimed in claim 1, wherein the proportion of macropores in the catalyst is at least 80% and the total pore volume is at least 0.1 ml/g.

4. A process as claimed in claim 1, wherein the hydrogenation is carried out continuously over a fixed bed of catalyst.

5. A process as claimed in claim 4, wherein the hydrogenation is carried out in the upflow or downflow mode in a flow tube.

6. A process as claimed in claim 1, wherein the nitrile to be hydrogenated is present as a solution in an organic solvent.

7. A process as claimed in claim 6, wherein the solvent used is dimethylformamide or N-methylpyrrolidone.

8. A process as claimed in claim 1, wherein the hydrogenation is carried out in the presence of ammonia.

9. A process as claimed in claim 1, wherein the hydrogenation is carried out at from 25 to 125° C. and a pressure of from 10 to 300 bar.

10. A process as claimed in claim 1, wherein the nitrile is selected from the group consisting of extender nitrites and Michael adducts of acrylonitrile.

11. A process as claimed in claim 1, wherein the nitrile is selected from the group consisting of iminodiacetonitrile, nitrilotriacetonitrile, ethylenediaminetetraacetonitrile, biscyanoethylpiperazine, dimethylamino propionitrile, dimethylaminopropylaminopropionitrile, isophoronenitril imine and methoxypropionitrile.

12. A process for producing an activated, alpha-$Al_2O_3$-containing, macroporous Raney catalyst based on an alloy of aluminum and at least one transition metal selected from the group consisting of iron, cobalt and nickel, and, if desired, one or more further transition metals selected from the group consisting of titanium, zirconium, chromium and manganese, which comprises the steps in the order (a)–(f):

(a) preparing a kneadable composition comprising the alloy, a shaping aid, water and a pore former;

(b) shaping the kneadable composition to form a shaped body;

(c) calcining the shaped body;

(d) activating the calcined shaped body by treatment with aqueous alkali metal hydroxide solution;

(e) rinsing the shaped catalyst body with aqueous alkali metal hydroxide solution;

(f) rinsing the shaped catalyst body with water.

13. A macroporous Raney catalyst which can be produced by a process as claimed in claim 12.

14. A macroporous Raney catalyst as claimed in claim 13 having a proportion of macropores of at least 80% and a total pore volume of at least 0.1 ml/g.

* * * * *

UNITED STATES PATENT AND TRADEMARK OFFICE
CERTIFICATE OF CORRECTION

PATENT NO. : 6,677,486 B2
DATED : January 13, 2004
INVENTOR(S) : Ansmann et al.

It is certified that error appears in the above-identified patent and that said Letters Patent is hereby corrected as shown below:

Column 8,
Line 33, "nitrites" should be -- nitriles --.

Signed and Sealed this

Eleventh Day of May, 2004

JON W. DUDAS
*Acting Director of the United States Patent and Trademark Office*